United States Patent [19]
Shillington et al.

[11] Patent Number: 5,947,950
[45] Date of Patent: Sep. 7, 1999

[54] GEAR DRIVEN NEEDLE REMOVAL DEVICE

[75] Inventors: Randall S. Shillington, Carlsbad; David R. Millar, Orange; Rex O. Bare, Lake Forrest, all of Calif.

[73] Assignee: Med-Safe Systems, Inc., Oceanside, Calif.

[21] Appl. No.: 09/026,191

[22] Filed: Feb. 19, 1998

[51] Int. Cl.[6] .................................................. A61B 19/00
[52] U.S. Cl. ........................ 604/403; 600/573; 206/366; 206/370
[58] Field of Search .................................... 600/573, 576; 604/192, 198, 317, 403; 81/3.08, 3.29, 3.33; 215/235, 329, 356; 206/366, 370

[56] References Cited

U.S. PATENT DOCUMENTS

| | | | |
|---|---|---|---|
| 4,956,907 | 9/1990 | Bruno | 604/403 |
| 4,986,811 | 1/1991 | Thead et al. | 604/110 |
| 5,348,549 | 9/1994 | Brown et al. | 604/403 |
| 5,402,887 | 4/1995 | Shillington | 206/366 |
| 5,474,181 | 12/1995 | Shillington et al. | 206/370 |

FOREIGN PATENT DOCUMENTS

| | | | |
|---|---|---|---|
| 0426556 | 5/1991 | France | 604/403 |
| 3501043 | 7/1986 | Germany . | |

*Primary Examiner*—Max Hindenburg
*Attorney, Agent, or Firm*—Baker & Maxham

[57] ABSTRACT

A needle removal apparatus, comprises a support member having an elongated track formed therein, a carriage mounted in the track and moveable back and forth on the track, a coupling device mounted on the carriage and adapted for receiving and coupling to a needle hub, a drive for rotating the coupling device and unthreading the needle from the syringe collar upon movement with the guide along the track, and biasing means for normally biasing the carriage to one end of the track.

16 Claims, 4 Drawing Sheets

GEAR DRIVEN NEEDLE REMOVAL DEVICE

BACKGROUND OF THE INVENTION

The present invention relates to needle removal devices for syringes and other holders and pertains particularly to an improved extractor for quick and easy removal of needles from syringes and other holders.

A huge volume of hypodermic needles are used daily in the medical and health care industry throughout the world and must be disposed of safely. These used needles pose a major health problem to the medical personnel using them as well as others who may intentionally or accidentally come into contact with them. The safe and effective disposal of these hypodermic needles poses one of the greatest health and disposal problems for the medical and health care industry throughout the world.

Hypodermic needles are widely used for both injection of medication and for withdrawing blood samples for diagnostic purposes. In many cases the needle is removed from the holder or syringe and separately disposed of. In some cases, particularly certain blood drawing devices, the holder is reused. In these cases, it is essential that the needle be easily, quickly and safely removed without risk to the user.

The present common technique of drawing blood samples is by means of an evacuated tube and holder combination such as that sold under the trademark VACUTAINER by the Becton Dickinson Company. These blood collection assemblies comprise a tubular holder or barrel having a double needle on one end and receives an evacuated tubular chamber into which blood is collected. The needle has a threaded hub which threadably mounts it on one end of the tubular holder. The threads of the hub connect and disconnect from the holder with less than a full rotation. The hub also has external flutes which are used to grip and rotate the needle. These flutes are large enough that some satisfactory devices have been developed for quick and easy removal of the needles from the blood collection devices.

However needles for syringes typically have smaller hubs and flutes. Consequently, the devices developed for blood collectors are not satisfactory for the removal of a needle from a syringe. Therefore, there is an evident need for a simple and effective apparatus for the quick and easy removal of needles from syringes.

It is desirable that a simple, safe and effective apparatus for the quick easy removal of hypodermic needles from syringes and other holders be available.

SUMMARY OF THE INVENTION

In accordance with a primary aspect of the present invention an apparatus for removal of a needle from a holder comprises an elongated support structure having an elongated track formed therein, a carriage mounted in said track and moveable back and forth on said track, coupling means mounted on said carriage and adapted for receiving and coupling to a needle hub, means for rotating said coupling means and unthreading said needle from said syringe collar upon movement with said guide along said track, and biasing means for normally biasing said carriage to one end of said track.

BRIEF DESCRIPTION OF THE PREFERRED EMBODIMENTS

The above and other objects and advantages of the present invention will become apparent from the following description when read in conjunction with the accompanying drawings wherein.

DETAILED DESCRIPTION OF THE PREFERRED EMBODIMENTS

Figure 1:
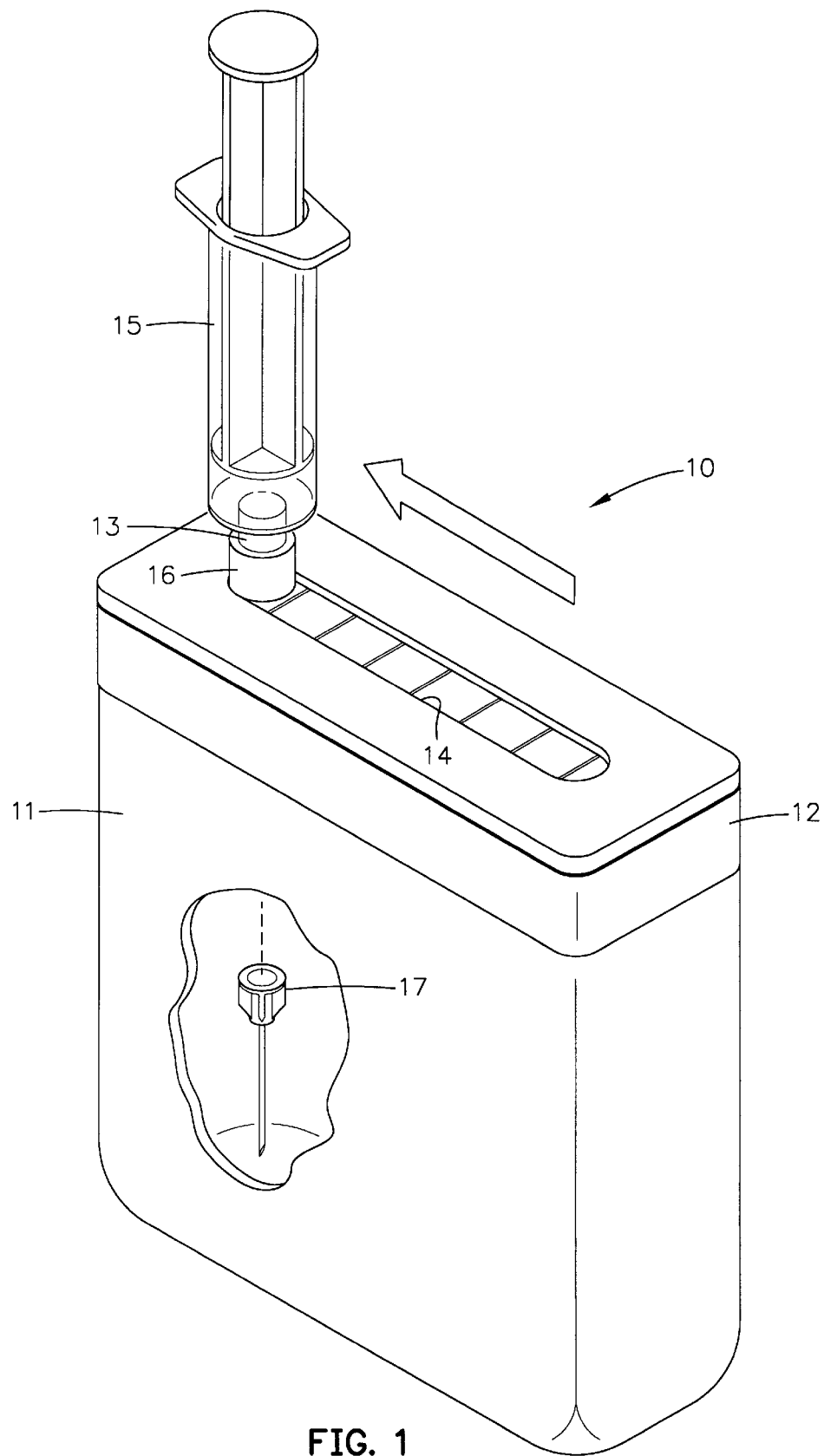
FIG. 1 is a perspective view of an exemplary embodiment of the present invention embodied in a disposable container.

Referring now to the drawings, and particularly to FIG. 1, there is illustrated a needle removal apparatus designated generally at 10, constructed in accordance with an exemplary embodiment of the present invention mounted on top of a disposable container 11. The apparatus comprises a housing of a generally rectangular box like configuration 12. The housing has an elongated slot 14 in the top thereof from which a tubular guide sleeve 16 extends vertically for receiving a syringe collar 13 of a syringe 15 for holding it in a predetermined orientation. The guide sleeve 16 is mounted on a moveable carriage within the housing 12 containing means for unthreading a needle hub 17 from the syringe body 15 when the collar is inserted therein and the syringe pulled along the length of the slot 14, as will be explained.

Figure 2:
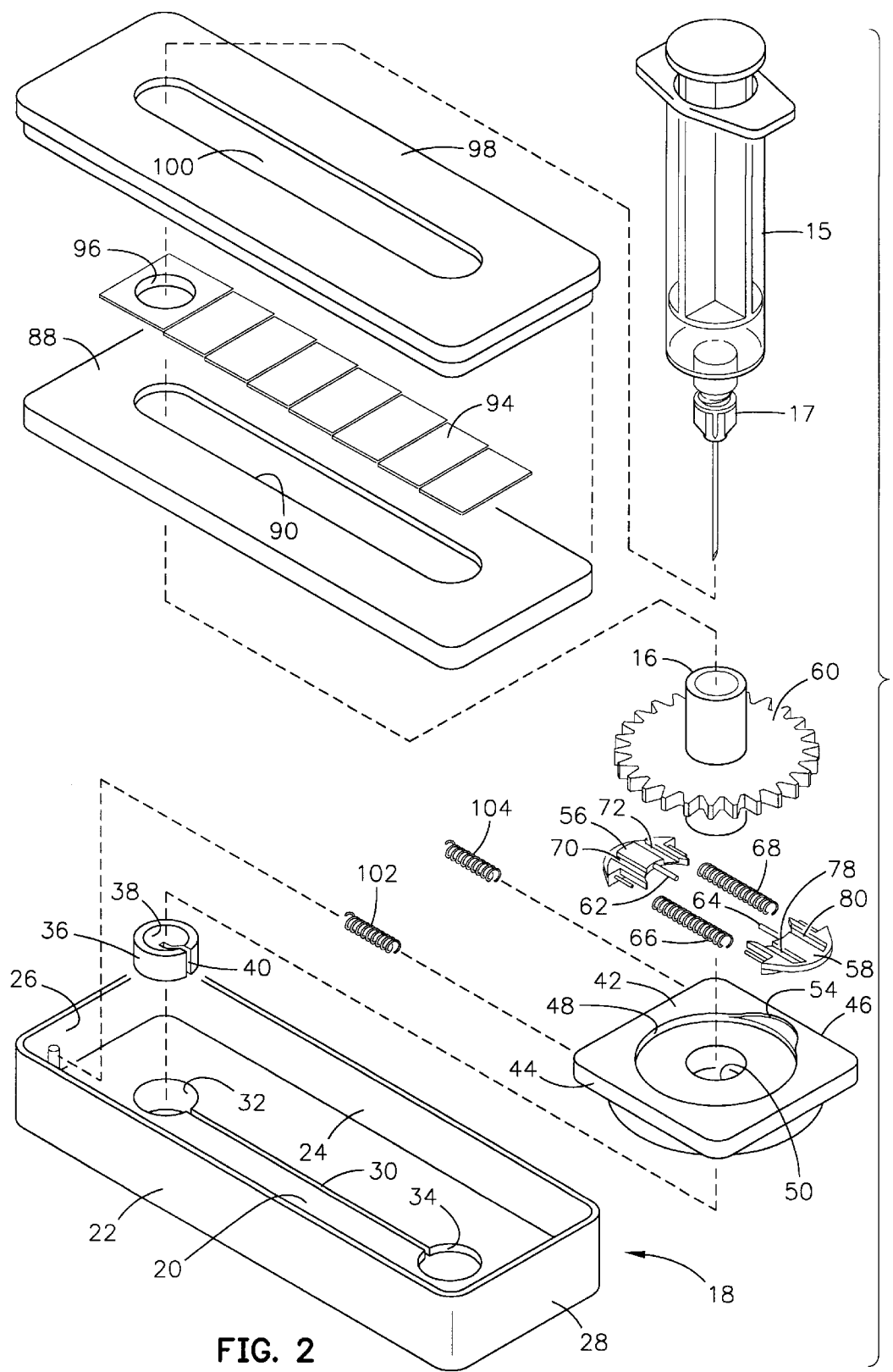
FIG. 2 is a perspective exploded view of the needle removal apparatus of FIG. 1.

Referring to FIG. 2 of the drawings, an exploded assembly view of the apparatus is illustrated. The illustrated embodiment comprises an elongated generally rectangular open top lower housing support structure 18. The housing has a bottom 20 with upstanding parallel opposed side walls 22 and 24 with end walls 26 and 28. The bottom 20 is provided with an elongated slot 30 that connects between a throughbore 32 and a throughbore 34. A needle guide 36 is mounted in the throughbore 32 for receiving and guiding a needle into the slot 30. The needle guide 36 is preferably a metal cylinder with an upper conical depression 38 with a side opening or slot 40 that mates with the slot 30. This needle guide marks the beginning end of the track of the device and guides a needle into slot 30.

A slider or carriage 42 having a generally square or rectangular upper portion has a pair of side walls or surfaces 44 and 46 which engage side walls 22 and 24 and are guided thereby along the length of the housing 18. Thus, the housing forms an elongated linear track for the carriage. The upper surface of the carriage 42 is formed with an upper generally cylindrical bore 48 which is concentric with a lower throughbore 50. The upper bore 48 is formed with upper and lower scalloped cut-outs or recesses 52 (FIG. 4) and 54 disposed on opposite sides and at different levels (i.e. upper and lower) within the bore 48. A pair of slides or cam followers 56 and 58 are adapted to mount in the bore 48 of the carriage and are rotatably coupled to a driving gear 60. The followers 56 and 58 carry pins or teeth 62 and 64 directed inwardly at their inner ends for engaging and coupling to the splines on the hub of a syringe needle. The followers are biased apart by a pair of compression springs 66 and 68 and are confined to an inner gripping position by the cylindrical wall of bore 48. The followers are biased into engagement with the wall of bore 48 and into cutouts 52 and 54 at certain positions of rotation to withdraw pins 62 and 64 from their engaging or coupling position.

Figure 3:
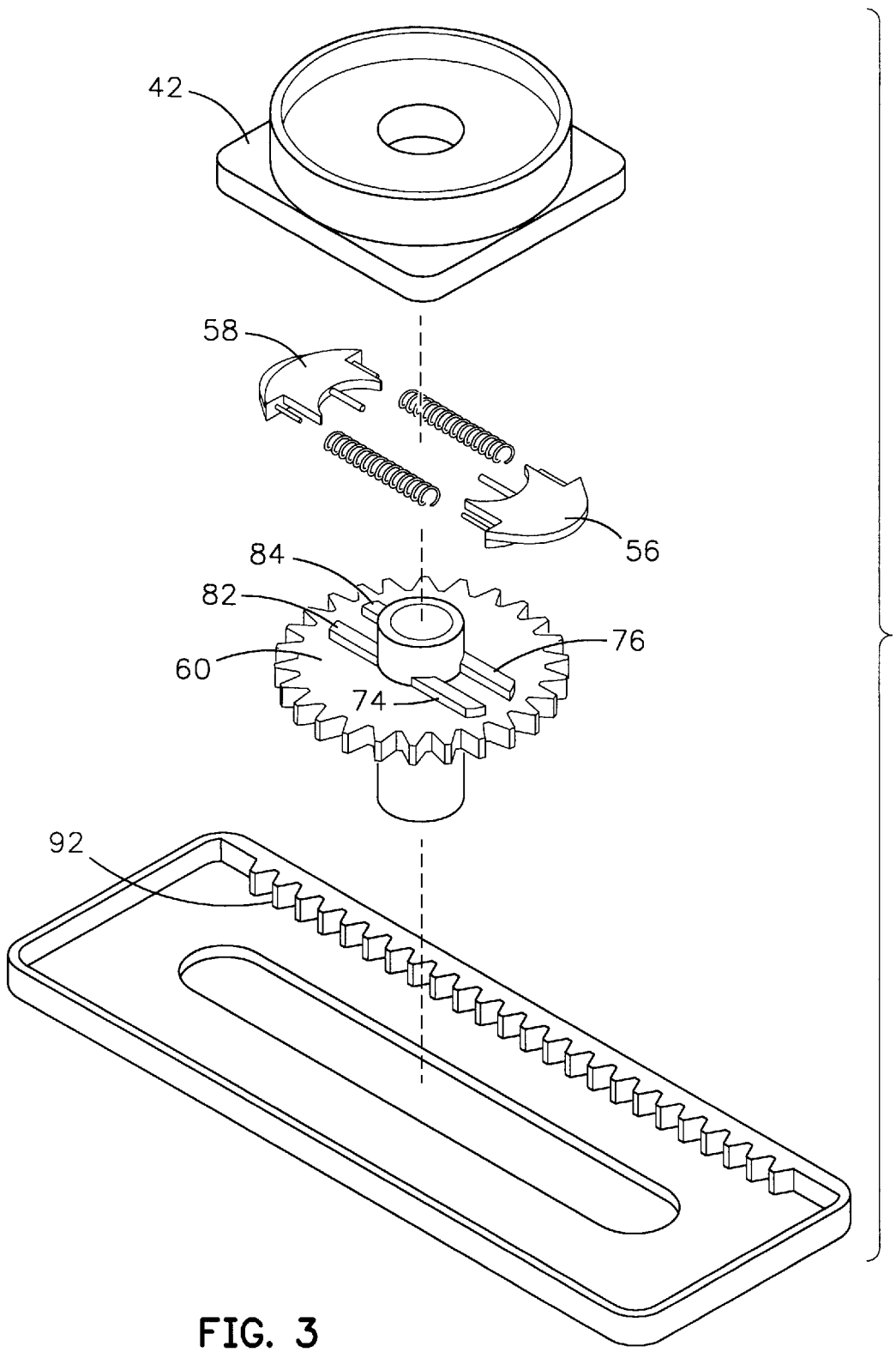
FIG. 3 is an inverted perspective exploded view of the gripping assembly of the needle removal apparatus of FIG. 1.

The followers 56 and 58 are coupled to the gear 60 by means of a pair of slots 70 and 72 on follower 56 engaging a pair of bars 74 and 76 on the bottom of gear 60, as can be seen in FIG. 3. The follower 58 is coupled by slots 78 and 80 to bars 82 and 84 on the underside of the gear 60. The gear 60 has an integral lower tubular extension 86 which is rotatably mounted in the bore 50 in the center of carriage 42. Upon rotation of the gear 60 the followers 56 and 58 rotate with the gear from the starting point or end of the housing and when they reach a point where cutouts 52 and 54 are located, they retract into the cutouts withdrawing the needle hub gripping the teeth or pins 62 and 64 from engagement with the flutes of the needle hub, allowing the needle to fall downward through opening 34 at the end of slot 30. The upper tubular guide 16 is also an integral coaxial extension of gear 60.

A rectangular cover panel member 88 fits down over the aforementioned assembly and into the housing 18 and includes an elongated slot 90 aligned over slot 30 and extending along the length thereof, through which the tubular guide sleeve 16 extends. The cover member 88 is also provided with an elongated rack or linear gear 92 (FIG. 3) along a lower side edge thereof for meshing with gear teeth on the pinion gear 60 for forcing rotation of the gear as the gear is carried along with the carriage in movement from one end to the other of the housing. The gear functions to rotate the needle hub gripping or engaging members and unthread a needle from a syringe body as the carriage goes from one end to the other of the housing.

A multi-plate seal 94 has an opening 96 through which the tubular guide 16 extends. The seal is of a general type well known in the automotive industry to go around shifting levers, for example, and comprises a plurality of plates stacked one on top of the other, each with a larger slot such that the entire mass of plates are progressively engaged and carried along with the movable member 16. A cover 98 includes an elongated slot 100 and encloses the entire assembly within the housing.

In operation when it is desired to remove a needle from a holder, the needle is extended down through the tubular guide 16 (FIG. 1) such that the neck 13 of the syringe extends into and is closely held in vertical alignment by the guide 16 while the needle extends down through and is guided by the guide 36 into position for movement along the slot 30. The splines on the hub of the needle are engaged by the pin or teeth 62 and 64 of the followers members 56 and 58 (FIGS. 4–6) and as the barrel of the syringe is pulled along the housing along the slot, the gear 60 begins to rotate carrying the followers and pins with it, and as it rotates it rotates the hub and unthreads the needle, permitting it to drop from the housing through opening 34 at the opposite end of the device.

Figure 4:
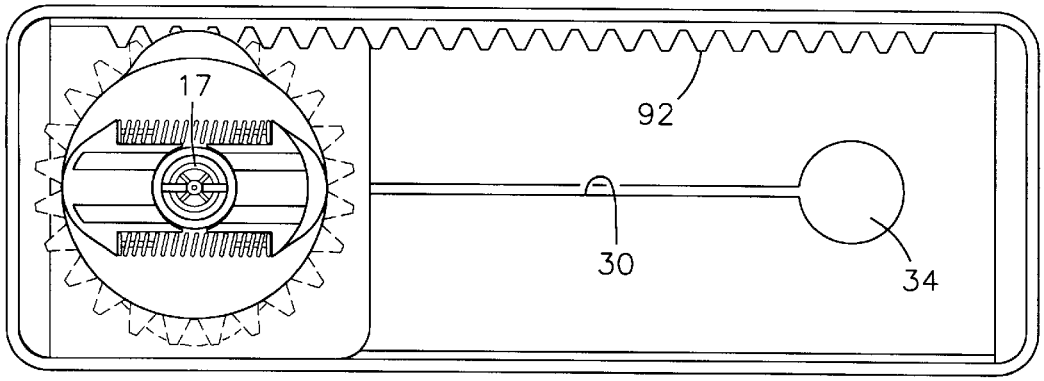
FIG. 4–6 are top plan views showing progressive stages of operation of the apparatus of FIG. 1.
Figure 5:
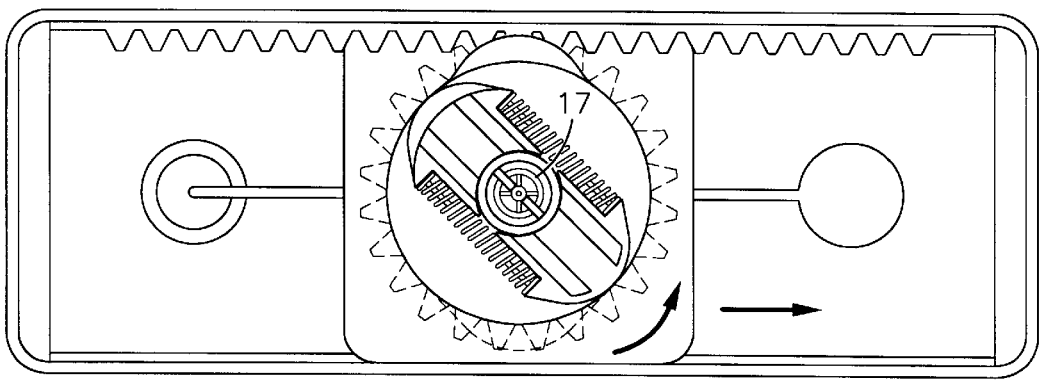
Figure 6:
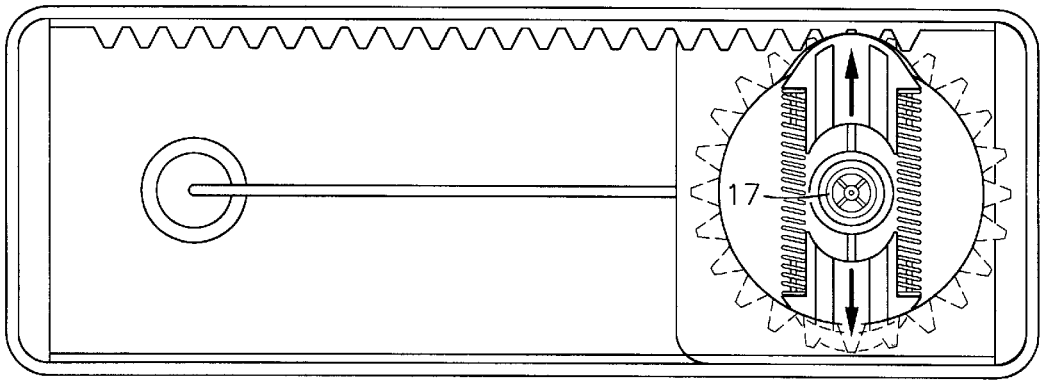

Referring to FIGS. 4, 5 and 6, a better understanding of operation of the device can be seen. As shown in FIG. 4, the carriage with the gripping mechanism is illustrated with the rotary gear 60 removed with only the teeth of the pinion, shown in phantom to aid understanding of the construction and operation. As shown in FIG. 4, the carriage is biased to the left-most position by means of a suitable spring or springs 102 and 104 (FIG. 2), such as a coil compression or tension springs. The coupling mechanism is rotatably adjusted to start from this position. When a needle is inserted into the guide, the needle extends down through and its spline is engaged by the two opposing pins or teeth on the opposing followers which are biased inward as shown, to engage between the splines of the needle hub. The gripping followers are shown in a position such that they each rotate approximately or move through an angle of approximately 270 degrees before engaging or arriving at cutouts where they each pop into or are biased outward into the recess or cutout, as shown in FIG. 6, thereby pulling or retracting the needles from the guide. This also retracts the pins from the splines of the hub so that the needle drops downward into a suitable container. It is apparent that the unthreading followers can be rotated in any number of ways, such as by a cord attached to the fixed housing on one end and wrapped around a drum coupled to or formed on the gear. Thus, movement of the slide along the track would result in rotation of the entire guide and hub gripping assembly.

The needle unthreading device may be a portable unit adaptable to be detachably attached to disposable containers or it may be built into the containers and be a part of it. In the alternative, it may be built into a holder to which disposable containers are mounted for receipt of the needles as they are removed from the syringes. Most syringes employ what is called a Luer lock for connection of the needle to the barrel of the syringe. The Luer lock is similar to threads with a shallow pitch and requires less than a full revolution for complete attachment and detachment. Typically, it requires about one half to slightly more than one half of a turn. Accordingly, the apparatus of the present invention may be adjusted to accommodate the Luer lock type connectors or a threaded connector as some needle holders employ. In the instant invention, the gripper pins are in the innermost gripping position for approximately 270 degrees of rotation of the gripper mechanism. Upon about 270 degrees of rotation, the followers are biased into the cutouts withdrawing the pins from engagement with the needle hubs, thereby allowing the needle hub to fall into the receptacle.

While we have illustrated and described our invention by means of specific embodiments, it is to be understood that numerous changes and modifications may be made therein without departing from the spirit and scope of the invention as defined by the claims.

We claim:

1. An apparatus for removal of a needle from a holder comprising:

an elongated support structure having an elongated track formed therein;

a carriage mounted in said track and moveable back and forth on said track;

coupling means mounted on said carriage and adapted for receiving and coupling to a needle hub;

means for rotating said coupling means and unthreading said needle from said syringe collar upon movement with said guide along said track; and biasing means for normally biasing said carriage to one end of said track.

2. An apparatus according to claim 1 wherein said means for rotating said coupling means comprises a gear train.

3. An apparatus according to claim 2 wherein said gear train comprises a rack extending along said track and a pinion on said coupling means in driving engagement with said rack.

4. An apparatus according to claim 3 wherein said coupling means comprises a pair of opposed pins positioned for engaging a spline on a hub of a needle.

5. An apparatus according to claim 1 wherein said coupling means comprises a pair of opposed pins positioned for engaging a spline on a hub of a needle.

6. An apparatus according to claim 5 wherein said carriage includes guide means adapted for receiving and holding a syringe collar in a predetermined orientation for positioning to a needle hub in said coupling means for coupling to the needle hub.

7. An apparatus according to claim 6 wherein said means for rotating said coupling means comprises a gear train.

8. An apparatus according to claim 7 wherein said gear train comprises a rack extending along said track and a pinion on said coupling means in driving engagement with said rack.

9. An apparatus according to claim 8 wherein said coupling means comprises a generally cylindrical internal wall having an upper and a lower recess and defining a generally cylindrical cavity;

a pair of spaced apart opposed followers disposed in said cylindrical cavity and confined by said walls to a normally inner position;

spline engaging means on an inner end of each of said followers adapted to engage a spline on a hub of a needle in said inner position; and means biasing said followers away from one another so that upon rotation of said followers to predetermined positions an outer end of said followers enter said respective upper and lower recesses and release a needle hub.

10. An apparatus according to claim 9 wherein said spline engaging means in a pin.

11. An apparatus according to claim 9 wherein said cylindrical cavity is formed in said carriage.

12. An apparatus according to claim 11 wherein said biasing means comprises a coil spring in tension between said followers.

13. A needle removal apparatus according to claim 9 wherein a guide is disposed above and aligned with coupling means mounted on said carriage, said guide means adapted for receiving and holding a syringe collar in a predetermined position and orientation to enable said coupling means coupling to a needle hub.

14. An apparatus according to claim 1 wherein a guide is disposed above and aligned with coupling means mounted on said carriage, said guide means adapted for receiving and holding a syringe collar in a predetermined position and orientation to enable said coupling means coupling to a needle hub.

15. An apparatus for removal of a needle from a holder comprising:

an elongated support structure having an elongated track formed therein;

a carriage mounted in said track and moveable back and forth on said track;

coupling means mounted on said carriage and adapted for receiving and coupling to a needle hub;

a guide is disposed above and aligned with coupling means, said guide means adapted for receiving and holding a syringe collar in a predetermined position and orientation to enable said coupling means coupling to a needle hub;

means for rotating said coupling means and unthreading said needle from said syringe collar upon movement with said guide along said track; and biasing means for normally biasing said carriage to one end of said track.

16. An apparatus according to claim 15 wherein coupling means comprises a generally cylindrical internal wall having an upper and a lower recess and defining a generally cylindrical cavity;

a pair of spaced apart opposed followers disposed in said cylindrical cavity and confined by said walls to a normally inner position;

spline engaging means on an inner end of each of said followers adapted to engage a spline on a hub of a needle in said inner position; and means biasing said followers away from one another so that upon rotation of said followers to predetermined positions an outer end of said followers enter said respective upper and lower recesses and release a needle hub.

* * * * *